US009347807B2

(12) United States Patent
Ao et al.

(10) Patent No.: US 9,347,807 B2
(45) Date of Patent: May 24, 2016

(54) MULTI-PHASE ULTRASONIC PIPE FLOW METER

(71) Applicant: General Electric Company, Schenectady, NY (US)

(72) Inventors: Xiaolei Shirley Ao, Lexington, MA (US); Oleg Alexander Khrakovsky, Lynn, MA (US); Yue Ma, Burlington, MA (US); Shawn Li Doria, North Billerica, MA (US); Jin Chang Xu, Andover, MA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 861 days.

(21) Appl. No.: 13/677,338

(22) Filed: Nov. 15, 2012

(65) Prior Publication Data

US 2014/0136126 A1     May 15, 2014

(51) Int. Cl.
| | |
|---|---|
| *G01F 1/74* | (2006.01) |
| *G01N 9/36* | (2006.01) |
| *E21B 49/08* | (2006.01) |
| *G06F 17/40* | (2006.01) |
| *G06F 19/00* | (2011.01) |
| *G01F 1/66* | (2006.01) |
| *G01N 9/00* | (2006.01) |

(52) U.S. Cl.
CPC .. *G01F 1/66* (2013.01); *G01F 1/74* (2013.01); *G01N 9/00* (2013.01); *G01N 9/36* (2013.01); *E21B 49/08* (2013.01); *G01N 2291/024* (2013.01); *G01N 2291/02818* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | | |
|---|---|---|---|---|---|
| 2,883,255 | A | * | 4/1959 | Anderson | B41J 11/36 340/518 |
| 2,961,539 | A | * | 11/1960 | Egan | G01V 5/12 250/269.3 |
| 3,371,527 | A | * | 3/1968 | Moulin | E21B 47/10 166/250.01 |
| 4,496,287 | A | * | 1/1985 | Nelson | F04B 17/046 417/417 |

(Continued)

FOREIGN PATENT DOCUMENTS

| | | |
|---|---|---|
| EP | 2343547 A2 | 7/2011 |
| WO | 2007022492 A1 | 2/2007 |
| WO | WO 2014/078471 A1 * | 5/2014 |

OTHER PUBLICATIONS

PCT Search Report and Written Opinion dated Feb. 25, 2014 issued in connection with corresponding PCT Patent Application No. PCT/US2013/069984.

*Primary Examiner* — Edward Cosimano
(74) *Attorney, Agent, or Firm* — Cooper Legal Group, LLC (57) ABSTRACT

A system for determining densities and proportions of phases in a multi-phase fluid flow (MFF) that can include an oil phase, a water phase, and a gas phase from a well. The system includes a first density sensor that senses the MFF at locations where the phases of the MFF are often separated, a second density sensor senses the MFF from the output of a phase mixer-homogenizer, and a third density sensor that senses, in real time, the MFF where the gas phase starts to separate or has separated from the liquid phase but where the liquid phases have not separated. The system also includes one or more processors for executing one or more programs to determine a density of the oil phase, a density of the water phase, a density of the gas phase, and proportions of phases including a water cut and a gas volume fraction based on readings from the first, second, and third density sensors.

20 Claims, 7 Drawing Sheets

(56) References Cited

U.S. PATENT DOCUMENTS

| | | | | | |
|---|---|---|---|---|---|
| 5,375,465 | A | * | 12/1994 | Carlson | G01N 33/241 73/152.05 |
| 7,343,820 | B2 | * | 3/2008 | Gysling | G01F 1/66 73/861.23 |
| 7,389,687 | B2 | * | 6/2008 | Gysling | G01F 1/666 73/200 |
| 7,437,946 | B2 | * | 10/2008 | Gysling | G01F 1/66 73/861.23 |
| 7,526,966 | B2 | * | 5/2009 | Gysling | G01F 1/667 73/861.23 |
| 2006/0096388 | A1 | | 5/2006 | Gysling et al. | |
| 2006/0266127 | A1 | | 11/2006 | Gysling et al. | |
| 2007/0001028 | A1 | * | 1/2007 | Gysling | G01F 1/66 239/318 |
| 2007/0157737 | A1 | * | 7/2007 | Gysling | G01F 1/667 73/861.23 |

\* cited by examiner

MULTI-PHASE ULTRASONIC PIPE FLOW METER

BACKGROUND OF THE INVENTION

1. Field of the Invention

The invention relates to determining densities and proportions of phases in a multi-phase fluid flow (MFF) that can include an oil phase, a water phase, and a gas phase from a well. The invention also relates to using the densities and proportions of the phases with flow sensors to determine the quantity output of the phases.

2. Discussion of Prior Art

Measurements of the outputs of oil and gas wells require a measurement system that accounts for the individual components of a multi-phase fluid flows (MFFs). The individual components include a gas phase, a water phase, and an oil phase. In some measurement systems, the different phases are separated and individually measured to determine the proportions between the phases and the output quantities, in volume or mass, of the phases. However, separation is an expensive process that is not cost effective for smaller land based wells that produce smaller quantities of energy. Alternatively, phase mixer-homogenizers are used as a less expensive alternative to separators when measuring the outputs of a MFF coming from a well. Phase mixer-homogenizers reduce the complexity of the mathematical equations used in calculating the output measurements of the phases by reducing the number of variables in the output equations. For example, when the three phases of gas, oil, and water come from a well they are usually partially separated in what is called a slug flow or stratified flow with the gas phases traveling quickly and slowly flowing liquid phases. To measure the flow rate of this type of separated MFF, the velocity of each phase has to be individually measured. However, a phase mixer-homogenizer creates a blended flow or uniform MFF with all of the phases traveling at the same velocity or flow rate. Therefore, with a phase mixer-homogenizer only one flow rate has to be measured because all of the phases travel at the same velocity. In contrast, with a separator three different flow rates need to be measured.

Density measurements of the different phases are important when solving for the outputs of the different phases from an oil or gas well. The density measurements are used to calculate the proportions between the different phases of gas, oil, and water. For example, density measurements are used to calculate the gas volume fraction of the MFF which is the proportion of gas in the MFF. Density measurements are also used to calculate the water cut of the MFF which is the ratio of water to oil in the MFF. These proportions can be combined with the single flow rate of the blended mixture of the MFF, from the output of the phase mixer-homogenizer, to determine the quantity outputs of the gas phase, the water phase, and the oil phase.

Additionally, density measurements are used to determine the proportions of phases even when the proportions are not used with flow rates to solve for the output quantities. The proportions of the different phases are used by the oil and gas industry to adjust different production inputs for oil and gas wells to optimize the production of the individual well or to optimize the production of an entire field of wells. Inputs into gas and oil wells may include: pressure, quantity of water input into the well, and the energy expenditure in pumping. Thus, density measurements of oil and gas wells are also an important because phases proportions alone, without flow metering, are useful for optimizing inputs into oil and gas wells.

However, traditional MFF density meters are too expensive to be used continuously with most small to mid-sized oil and gas wells that are land based. Therefore, traditional MFF density meters are configured as portable units to be used with multiple oil wells. This requires a crew to attach and move the density sensors, and thus portable density sensors increase labor expenses. Traditional MFF density meters also emit radiation, including X-rays and gamma rays. Additionally, traditional MFF density meters are only attached to an oil well periodically, usually with an interval of months between measurements. Changes in the outputs of an oil well or oil field, such as changes in proportions of phases, are not readily detected in these situations due to the long periods between density measurements on the wells. Frequent density measurements are necessary to determine changes in the phase proportions which are used to optimize production inputs of the oil well. Frequent density measurements also improve the accuracy of the quantity outputs (e.g. volume or mass) of the different phases because frequent density measurement accounts for changes in the proportions between the phases which affect the accuracy of the output quantity calculations. Many smaller output land based oil wells could use an inexpensive, non-radiation emitting, and permanent meter for measuring MFF densities to detect changes, thus increasing the ability to optimize production from an oil well, make fast business decisions, while also increasing safety.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

One aspect of the invention provides a system for determining densities and proportions of phases in a multi-phase fluid flow MFF that can include an oil phase, a water phase, and a gas phase from a well. For the purposes of the application, it is understood that the term MFF may refer to a three-phase fluid flow. The system includes a first density sensor that senses, in real time, a plurality of first density profiles of the MFF at a first location where phases of the MFF are separated for, at least, short intervals of time. The system also includes a second density sensor that senses a plurality of second density profiles of the MFF at a second location where the MFF is a blended mixture of, at least, the oil phase, the water phase, and the gas phase. The system further includes a third density sensor that senses, in real time, a plurality of third density profiles of the MFF at a third location where the gas phase is separate from a mixed liquid portion of the MFF that includes, at least, the water phase and the oil phase. The system may also include one or more processors for executing one or more programs to determine a density of the oil phase, a density of the water phase, a density of the gas phase, and proportions of phases including a water cut and a gas volume fraction based on at least the plurality of first, second, and third density profiles.

Another aspect of the invention provides a method for determining densities and proportions of phases in a MFF that can include an oil phase, a water phase, and a gas phase from a well. The method includes sensing, in real time, a plurality of first density profiles of the MFF using a first density sensor at a first location where phases of the MFF are, for at least short intervals of time, separated. The method also includes sensing a plurality of second density profiles of the MFF using a second density sensor at a second location where the MFF is a blended mixture of at least, the oil phase, the water phase, and the gas phase. The method further includes sensing, in real time, a plurality of third density profiles of the MFF using a third density sensor at a third location. The third location is where a gas phase of the MFF is separate from a mixed liquid portion of the MFF that includes at least the water phase and the oil phase. The method may also include analyzing, at least, the plurality of first density profiles, using transient analysis, and determining a density of the oil phase, a density of the water phase, and a density of the gas phase. The method may further include determining proportions of phases including a water cut and a gas volume fraction based on the plurality of first, second, and third density profiles.

Still another aspect of the invention provides a system for determining output quantities of phases in a MFF that includes an oil phase, a water phase, and a gas phase from a well. The system determines the output quantities of phases by determining densities and proportions of phases in the MFF. The system includes a first density sensor that senses, in real time, a plurality of first density profiles of the MFF at a first location where phases of the MFF are separated for, at least, short intervals of time. The system also includes a second density sensor that senses a plurality of second density profiles of the MFF at a second location where the MFF is a blended mixture of at least, the oil phase, the water phase, and the gas phase. The second location of the second density sensor may be at an output of a phase mixer-homogenizer that homogenizes the MFF into the blended mixture. The system further includes a third density sensor that senses, in real time, a plurality of third density profiles of the MFF at a third location where the gas phase is separate from a mixed liquid portion of the MFF that includes, at least, the water phase and the oil phase. The system also includes at least one flow sensor that senses a velocity of the blended mixture. The system may also include one or more processors for executing one or more programs to determine a density of the oil phase, a density of the water phase, a density of the gas phase, and proportions of phases based on at least the plurality of first, second, and third density profiles. The one or more processors for executing one or more programs is also to determine and output to a user one or more of an output quantity of the oil phase, an output quantity of the water phase, and an output quantity of the gas phase based, at least, on the velocity of the blended mixture, the density of the oil phase, the density of the water phase, the density of the gas phase, and the proportions of phases.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Example embodiments that incorporate one or more aspects of the invention are described and illustrated in the drawings. These illustrated examples are not intended to be a limitation on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

Figure 1:
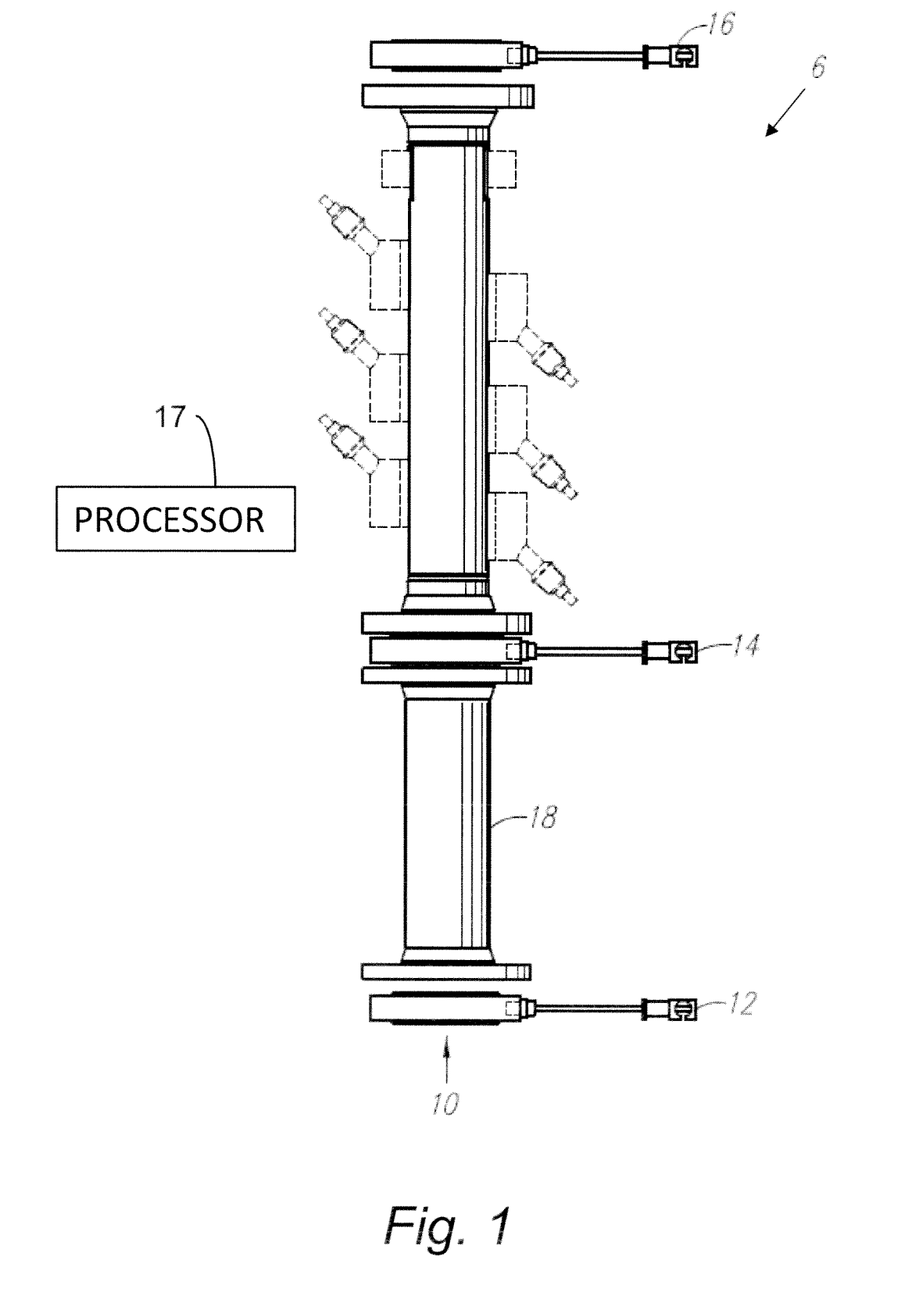
FIG. 1 is an example embodiment of a system for determining densities and proportions of phases in the MFF that can include an oil phase, a water phase, and a gas phase from a well.

An example embodiment of a system 6 for determining densities and proportions of phases in a multi-phase fluid flow (MFF) is shown in FIG. 1. The MFF includes an oil phase, a water phase, and a gas phase that come from a well 10 that may be a gas well, an oil well, or a petroleum well. At least three density sensors are included in system 6. The density sensors include a first density sensor 12, a second density sensor 14, and a third density sensor 16. Also included in system 6 is one or more processors 17 for running one or more programs. Optionally, a phase mixer-homogenizer 18 may also be included in the system 6. Alternatively, the system 6 may be used with an existing phase mixer-homogenizer 18 that is independent of system 6 or with another device that creates a uniform blended mixture of the MFF. In the example embodiment, the MFF flows from the first density sensor 12, through the phase mixer-homogenizer 18, to the second density sensor 14, and then to the third density sensor 16. It is understood that in other embodiments the order of the density sensors may be different from that shown in FIG. 1. The MFF from an oil or gas well may refer to a three-phase fluid flow of oil, water, and gas.

The first density sensor 12 is at a first location that is upstream of a phase mixer-homogenizer 18 where the MFF is separated for at least short intervals of time. The MFF is shown as flowing from a position upstream of the first density sensor 12 to a position downstream of the third density sensor 16. The MFF is a separated flow that may, for example, be a gas phase, followed by a water phase, followed by an oil phase, followed by a mixture of water and oil phases. This type of separated flow is commonly referred to as a slug flow. The first density sensor 12 senses in real time the separated flow and allows the sensor to capture profiles that correspond to the densities of the individual phases as they pass the sensor. Real time sensing allows the first density sensor 12 to be used for determining the individual densities of the different phases of the MFF (e.g. gas, oil, and water) in a separated or slug flow coming from an oil or gas well. This is accomplished without performing the expensive procedure of separating the different phases. An example of density profiles from the first density sensor 12 is described below with regards to FIG. 7.

Sensing in real time includes sensing a density profile instantaneously to detect the densities of the different phases while they are separated. Real time density sensing also can be used to detect the densities of mixtures of the different phases. For example, the density of a mixture of oil and water can be detected. In contrast, non-real time sensing merely sense average density profiles over longer lengths of time and cannot be used to detect the different phases and/or different phase mixtures in a separated MFF.

The second density sensor 14 is placed at a second location where the MFF is a blended mixture of at least, the oil phase, the water phase, and the gas phase. In the example embodiment, the second location is the output of the phase mixer-homogenizer 18. The phase mixer-homogenizer 18 mixes/blends the multiple phases of the separated MFF into a single, homogenized blended mixture that is no longer separated. The phase mixer-homogenizer 18 is also commonly used to equalize the velocities of the multiple (e.g., three) phases. However, the phase mixer-homogenizer 18 has the added benefit of providing the blended mixture for density sensing. By sensing the density of the blended mixture one can determine an average density of the MFF. The second density sensor 14 may be a real time sensor, like the first density sensor 12, or optionally it may be a slower average density sensor that does not respond quickly to changes and is not capable of sensing the separate phases of a separated flow coming from an oil well. Real time density sensing is used to determine the densities of the individual phases of the gas phase, the water phase, and the oil phase when the phases are separated. In contrast, the second density sensor 14 is used to determine the average density of the MFF when the flow is blended and does not require a real time density sensor.

The third density sensor 16 is at a third location downstream of the phase mixer-homogenizer 18. This downstream third location is where mixing is maintained between, at least, the water phase and the oil phase, which is known as the mixed liquid portion. However, this downstream third location is also where the gas phase separates from the mixed liquid portion after the blending process. This allows for a density measurement of the mixed liquid portion without the gas phase. In practice, this third location is at a distance slightly downstream of the phase mixer-homogenizer 18 because the gas phase separates from the blended mixture before the water and oil phases separate from each other. The distance downstream of the phase mixer-homogenizer 18 may be one or two circumferences of the output conduit or opening of the phase mixer-homogenizer 18.

The system 6 also includes one or more processors 17 for executing one or more programs to determine a density of the oil phase, a density of the water phase, a density of the gas phase, and proportions of phases including a water cut and a gas volume fraction based on at least the plurality of first, second, and third density profiles.

For example, by knowing the density of the mixture of the oil and water phases and the individual densities of oil and water, the one or more processors 17 can determine the proportion of water to oil, which is known as the water cut. By knowing the average density of the three phases (from the second density sensor 14) when the three phases are blended, by knowing the density of the gas phase (from the first density sensor 12), and by knowing the density of the mixed oil and gas phases, the one or more processors 17 can then determine the gas volume fraction which is the proportion of gas in the MFF. Once the gas volume fraction and the water cut are known, the proportion of the three phases relative to one another can be calculated by the one or more processors 17. Optionally, these proportions can be combined with a measurement from an optional flow sensor that measures the output of the phase mixer-homogenizer 18 to determine the output quantities of the phases.

The one or more processors 17 are operably connected (not shown) to the first density sensor 12, the second density sensor 14, and the third density sensor 16 to receive the information from the sensors related to the densities being sensed. The one or more processors 17 are also used to analyze the density profile information from each sensor, perform transient analysis on the density profile information, and determine the densities of the individual phases, the densities of the liquid portion (e.g. water and oil), and the average density.

It is to be understood that the system 6 depicted in FIG. 1 may or may not include the phase mixer-homogenizer 18. While the system 6 utilizes measurements from the blended mixture to compute its determinations, which are often associated with the output of a phase mixer or phase homogenizer, it is also possible that the blended mixture may come from another source. Additionally, the system 6 of FIG. 1 is not intended to limit the claims to only a system that includes or excludes the phase mixer-homogenizer 18.

An example of the MFF flowing through the system 6 for determining densities and proportions of phases in an MFF follows. A separated MFF (e.g. a slug flow) flows through the first density sensor 12 that measures the first density profiles used to determine the density profiles of gas, oil, and water. The MFF then flows through the phase mixer-homogenizer 18 that creates the blended mixture from the separated MFF, to the second density sensor 14 which measures the average density of the MFF by sensing the blended mixture. The MFF then flows through the third density sensor 16 which detects the flow as the gas phase is separated from the liquid portion of the phases (oil and water) to measure the density of the liquid portion.

Figure 2:
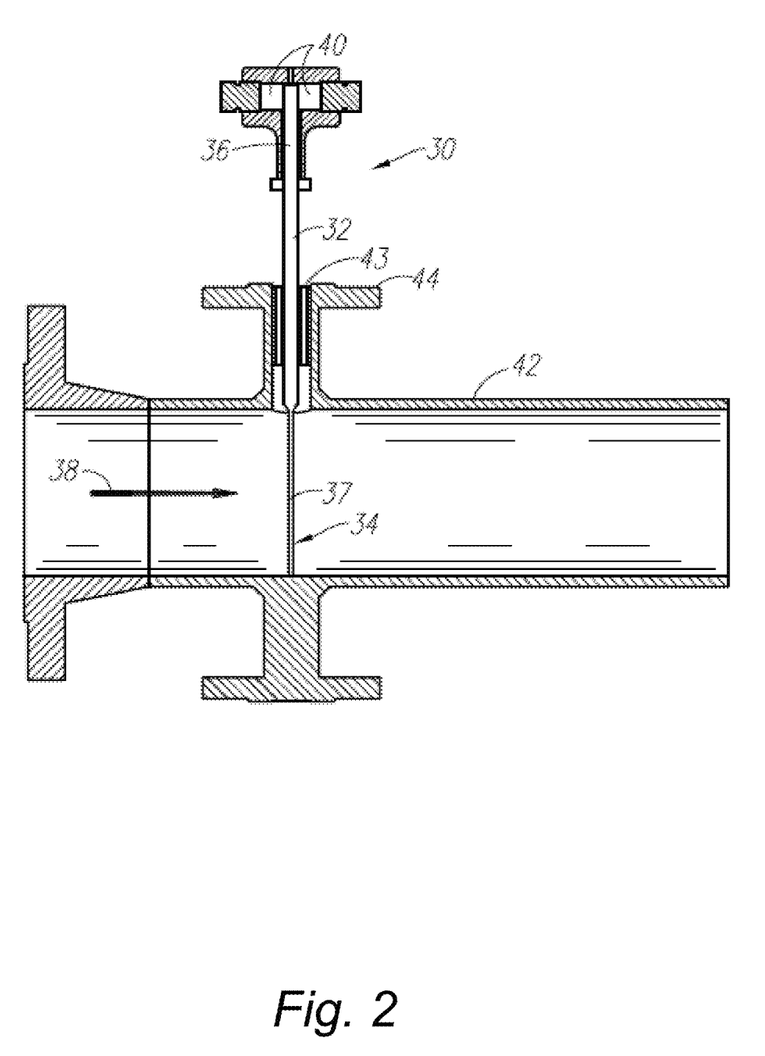
FIG. 2 is an example embodiment of an acoustic waveguide assembly mounted in an example environment.

Turning to FIG. 2, an example embodiment of an acoustic waveguide assembly 30 is shown in an example environment. The acoustic waveguide assembly 30 is an embodiment of the first density sensor 12, the second density sensor 14, and/or the third density sensor 16 and is shown mounted to pipe or conduit in an example environment. 2. At least one acoustic waveguide assembly 30 is used in a density sensor. However, it is understood the density sensors described in FIG. 1 are not limited to a single sensor. The acoustic waveguide assembly 30 includes a waveguide rod 32 having a proximal end 34 and a distal end 36. In the example environment, at least a portion of the waveguide rod 32 is immersed at location 37 in the flowing MFF 38. The acoustic waveguide assembly 30 also includes an waveguide sensor 40 connected to the distal end 36 of the waveguide rod 32 for sensing a plurality of time of flights of acoustic signals reflected off an end of the waveguide rod 32. The waveguide sensor 40 may optionally emit the acoustic signal that is being reflected. The acoustic signal is reflected off the proximal end 34 while another portion of the acoustic signal is reflected off another portion of the waveguide rod 32. By comparing the time of flights of the different reflected portions of an acoustic signal a density profile of the fluid passing the waveguide rod 32 can be measured. Alternatively, a comparison may be performed on different acoustic signals to obtain a density profile. This density profile may be used by the one or more processors 17 to calculate the density of the fluid that passed and was measured by the waveguide rod 32.

It is understood that the one or more processors 17 may include different processors in different locations. For example, each density sensor may have its own processor that is one of the one or more processors 17.

The acoustic waveguide assembly 30 of FIG. 2 is shown in an example environment mounted to a conduit 42 that conducts the MFF 38. The conduit 42 typically contains an MFF 38 under high pressure. Typically oil and gas wells in which the system 6 is utilized are usually maintained under high pressure to cause natural resources under the ground to rise to the surface. The system 6 may optionally be used in a pipeline that is kept under high pressure. The conduit 42 is a pipe or other container used to carry and/or contain the MFF. A high pressure coupler 43 connects the conduit 42 to the waveguide rod 32 and forms a high pressure seal between the interior portion of the waveguide rod 32, that is located within the conduit 42, and the exterior portion of the waveguide rod 32, that is located outside of the conduit. The waveguide sensor 40 is attached to the waveguide rod 32 and is typically located outside of the high pressure environment of the conduit 42. The example environment of the conduit 42 may optionally include a flange 44.

Figure 3:
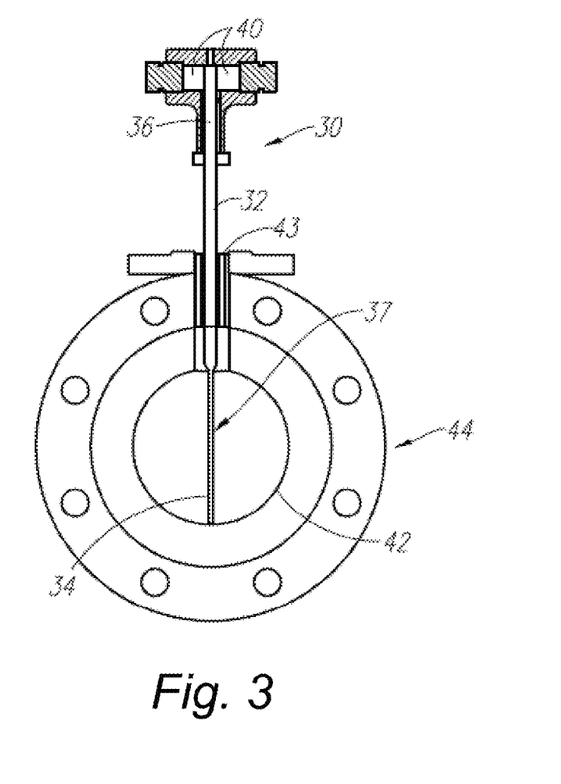
FIG. 3 is another perspective of the acoustic waveguide assembly of FIG. 2.

Turning to FIG. 3, another profile or perspective of the acoustic waveguide assembly 30 of FIG. 2 is shown. The acoustic waveguide assembly 30 of FIG. 3 is a view that is ninety degrees from the angle shown in FIG. 2.

Figure 4:
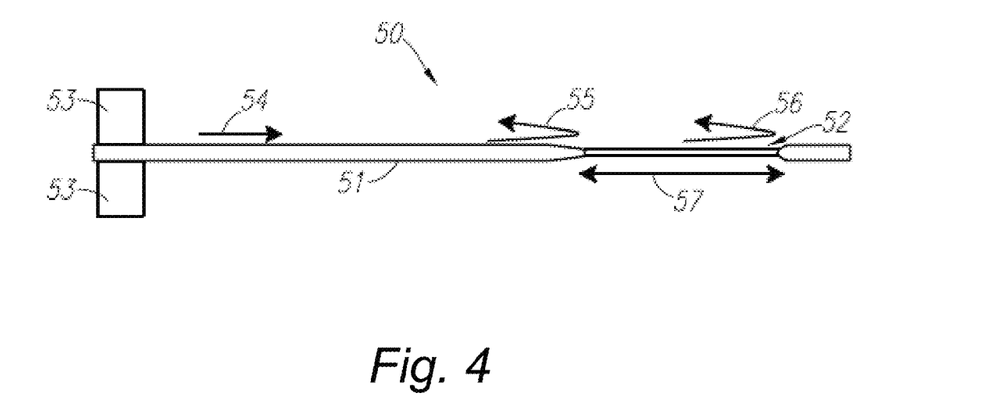
FIG. 4 is an example embodiment of a waveguide rod used in the acoustic waveguide assemblies of FIG. 2 and FIG. 3.

Turning to FIG. 4, an example embodiment of a waveguide rod 50 is shown. The waveguide rod 50 of FIG. 4 is another example of the waveguide rod 32 that was shown in FIG. 2 and FIG. 3 with the addition of acoustic signals to show the acoustic signals are measured in relation to the waveguide rod 50. Again, the acoustic signals of the waveguide rod 50 are used to determine the density profiles and the densities of the phases of the MFF as it passes the waveguide rod 50, which is immersed in the MFF 38 as shown in FIG. 2. The waveguide rod 50 has a first cross section 51 at the distal end and a second cross section 52 at the proximal end. A portion of the waveguide rod 50 is immersed in the flowing MFF. Specifically, the second cross section 52 is immersed in the MFF while the first cross section 51 is not immersed in the MFF. The first cross section 51 may also be partially immersed in the MFF. A waveguide sensor 53 emits an acoustic signal 54 which travels down the first cross section 51.

A first portion of the acoustic signal 55 reflects off of an end of the first cross section 51 to return to the waveguide sensor 53. The time between the emission of the acoustic signal 54 and the return of the first portion of the acoustic signal 55 to the waveguide sensor 53 is measured by the sensor and is known as the first time of flight. A second portion of the acoustic signal 56 reflects off the end of the second cross section 52 and returns to the waveguide sensor 53. The time between the emission of the acoustic signal 54 and the return of the second portion of the acoustic signal 56 is known as the second time of flight. It is understood that the first portion of the acoustic signal 55 and the second portion of the acoustic signal 56 can be portions of the same acoustic signal (e.g. acoustic signal 54) that is emitted from the waveguide sensor 53 or can be portions of different acoustic signals emitted from the waveguide sensor 53. In one example, the acoustic signal 54 is a torsional acoustic wave that travels on the exterior of the first cross section 51 and the second cross section 52.

By comparing the times of flight of the first portion of the acoustic signal 55 and the second portion of the acoustic signal 56 one can determine a density profile of the fluid or mixture of fluids that surrounds the waveguide rod 50 during the time of flights. For example, the waveguide sensor 53 senses the first time of flight of a first portion of the acoustic signal 55 which is typically used as reference signal to determine the speed of sound in the sensor under ambient conditions (e.g. temperature and pressure). This reference signal is used to account for variations in densities of the phases due to temperature that effect the time of flights. Then a compared time of flight 57 is determined by calculating the difference between the first time of flight and the second time of flight. The compared time of flight 57 is the time of flight of an acoustic wave in the MFF. The compared time of flight 57 corresponds to the density of the fluid surrounding the waveguide rod 50. The reference signal may be used to adjust the compared time of flight 57 to determine a density of the fluid in proximity to the waveguide rod 50.

Additionally, one may iteratively repeat the sending of the acoustic signal 54, the sensing of the first time of flight and the sensing of the second time of flight to obtain a plurality of time of flights that are used to determine a plurality of density profiles. The plurality of density profiles are discussed further below in the description of FIG. 7. The one or more processors 17 of FIG. 1 and FIG. 5 may be used to compare the first time of flights and the second time of flights to determine the compared time of flight 57. Alternatively, the times of flight may be compared in a processor that is included with the waveguide sensor 53 and then is shared with the one or more processors 17. The compared time of flight 57 (e.g. time of flight in the MFF) and the first time of flight (e.g. reference signal) are then used to determine a density profile.

Figure 5:
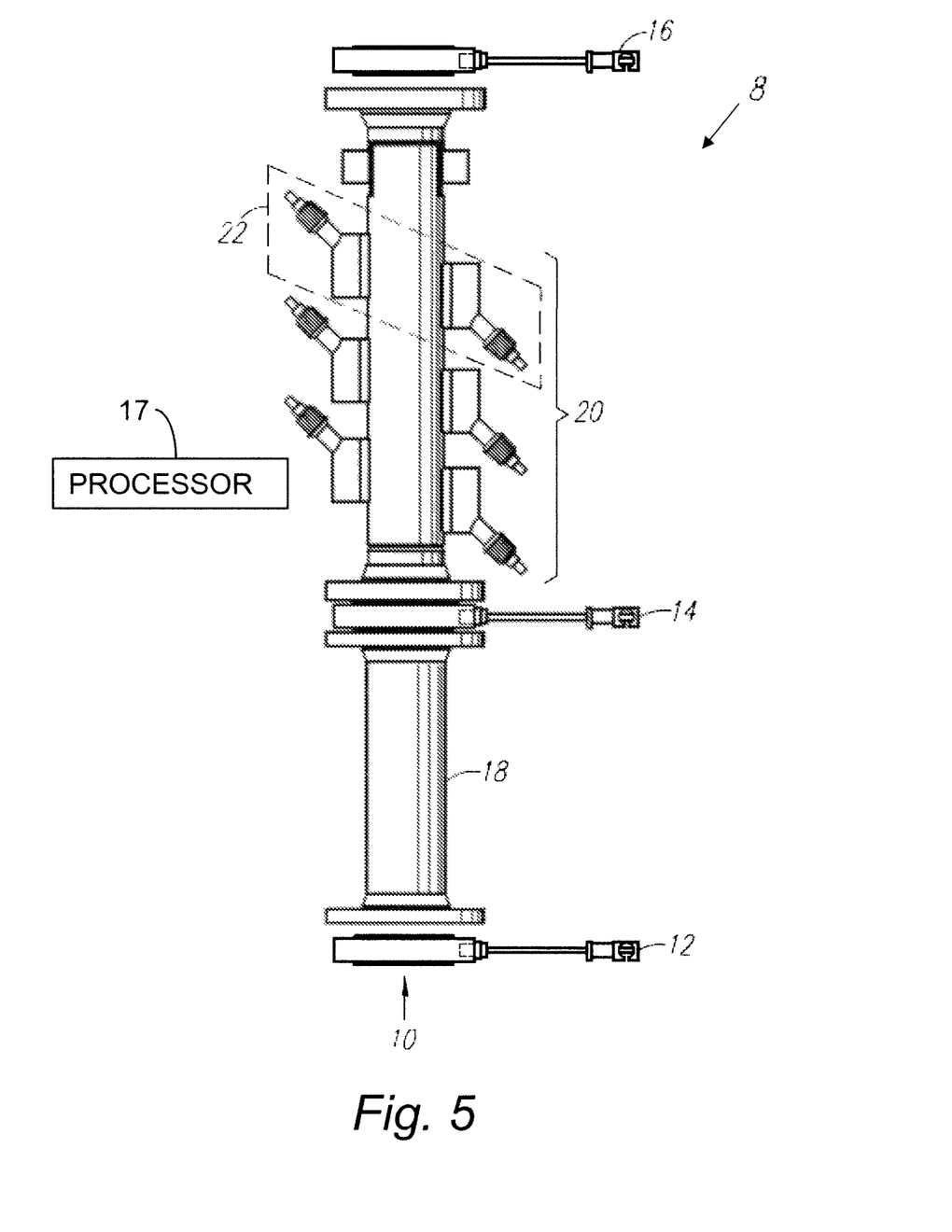
FIG. 5 is an example embodiment of a system for determining densities and proportions of phases in the MFF of FIG. 1 that also determines output quantities of phases in the MFF.

In another example embodiment, a system 8 for determining densities and proportions of phases in the MFF also determines output quantities of phases in the MFF, as shown in FIG. 5. The system 8 of FIG. 5 determines output quantities for an oil phase, a water phase, and a gas phase coming from a well 10 by determining densities and proportions of phases in the MFF, similar to system 6 of FIG. 1, but system 8 also measures the velocity or flow rate of the phases and computes the output quantities in volume or mass.

The system 8 of FIG. 5 is similar to the system 6 of FIG. 1. Both systems include a first density sensor 12, a second density sensor 14, and a third density sensor 16. Optionally, a phase mixer-homogenizer 18 may also be included in the system 8 of FIG. 5. The system 8 also includes one or more processors 17 that determine the phase densities and phase proportions based on the different phases densities. However, the system 8 of FIG. 5 also includes the additional feature of at least one flow sensor 20 for sensing a velocity of the blended mixture that comes from the phase mixer-homogenizer 18. In this embodiment, the at least one flow sensor 20 is placed at the output of the phase mixer-homogenizer 18 where the different phases of the MFF have uniform velocities. The at least one flow sensor 20 is operably connected to the one or more processors 17 (not shown) much like the density sensors.

The system 8 of FIG. 5 also includes the one or more processors 17 to determine an output quantity of the oil phase, an output quantity of the water phase, and an output quantity of the gas phase based, at least, on the phase densities, the phase proportions, and the velocity of the blended mixture. The output quantities may be, for example, volumetric quantities and/or mass quantities for a given period of time for the different phases. The output quantities of the phases may optionally be determined based on one or more of: a temperature of the MFF, a pressure of the MFF, a surface area and/or the cross section of the conduit conducting the MFF, the surface area or cross section of the at least one flow sensor 20, and other environmental factors measured in and around the MFF or the sensors. The at least one flow sensor 20 may be a pair of acoustic flow sensors 22 that are associated with FIG. 6, described below.

The one or more processors 17 for executing one or more programs also determines an output quantity of the oil phase, an output quantity of the water phase, and an output quantity of the gas phase. These output quantities are based, at least in part, on one or more of: the density of the oil phase, the density of the water phase, the density of the gas phase; the proportions of phases; the velocity and/or flow rate of the blended mixture; a pressure of the MFF inside the conduit, oil well, gas well, or phase mixer-homogenizer 18; and a temperature of the MFF. The system 8 may optionally include an interface to output to a user at least one of the output quantity of the oil phase, the output quantity of the water phase, and the output quantity of the gas phase.

It is understood that MFFs are often very complex, with the different phases in the flow travelling at different velocities. A brief discussion of MFFs as they relate to the flow sensor 20 of FIG. 5 is included to further assist the reader in understanding the calculations performed by the one or more processors 17 to determine the output quantities of the phases. Typically in pipeline and/or oil and gas well applications, a stratified flow or a slug flow would have high velocity gases and lower velocity liquids. Measurement of output quantities in this situation would require that the velocity of each individual phase (e.g. oil, water, and gas) be measured by separating the phases. This is difficult and expensive. However, if the slug flow is homogenized or blended by a phase mixer-homogenizer 18, all of the velocities of the different phases (including the gas phase, the oil phase, and the water phase) are uniform, and therefore only one velocity measurement of the MFF needs to be taken. In this environment, the velocity of the blended phases and the average density measurement, taken at the point where the MFF is blended, are both used to calculate the total output quantity of the MFF, including all the different phases. Then, the proportions or phase proportions, which may include the water cut and gas volume fraction, are used to determine the output quantities of the individual phases from the total output quantity of the MFF. In contrast, measuring the flow rate or velocity of the MFF with the at least one flow sensor 20 at the point where the MFF is blended decreases the complexity of the equations used to determine the output quantities of the phases by eliminating the need to measure the velocities of each phase separately. The phase mixer-homogenizer 18 also provides a blended mixture that can be sensed for determining the average density of the MFF with all three phases.

Figure 6:
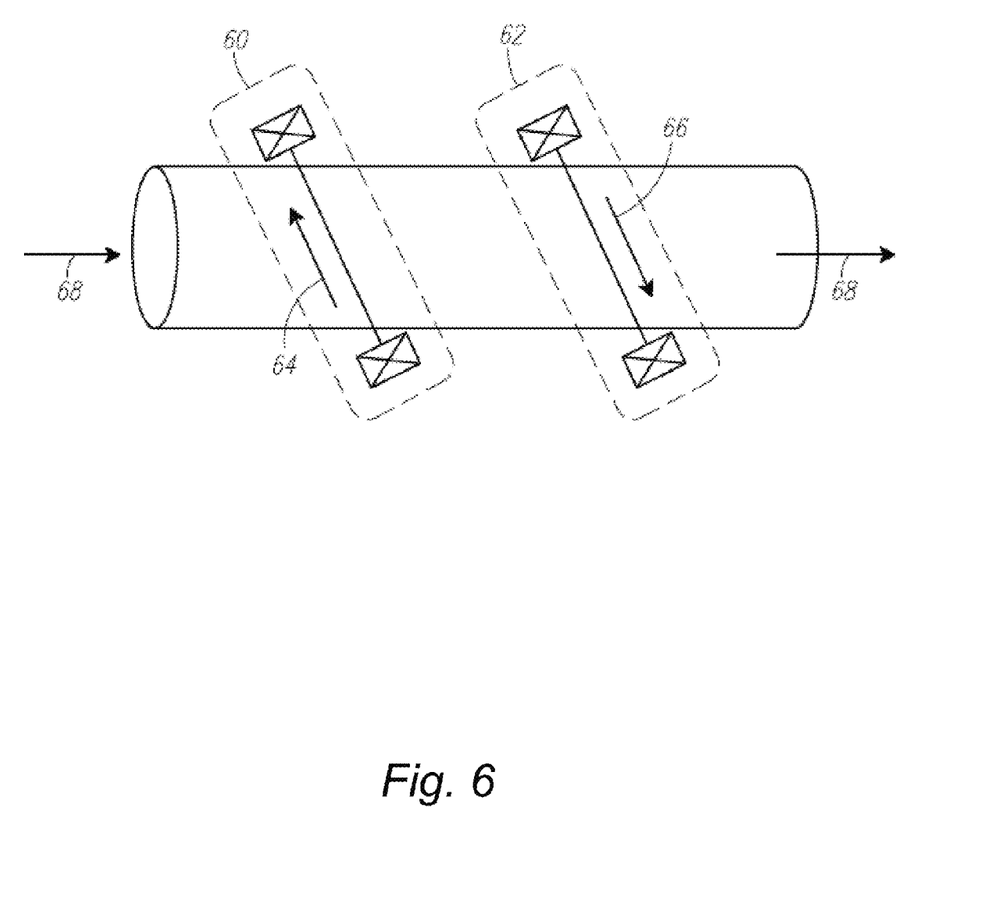
FIG. 6. is an example embodiment of an acoustic flow sensor for sensing the velocity or flow rate of the MFF.

Turning to FIG. 6, an example embodiment of a first acoustic flow sensor 60 and a second acoustic flow sensor 62 for measuring the velocity of a fluid flow are shown. The first acoustic flow sensor 60 and the second acoustic flow sensor 62 are example embodiments of the pair of acoustic flow sensors 22 of FIG. 5 that correspond to one of the at least one flow sensors 20 of FIG. 5. The first acoustic flow sensor 60 senses at least an upstream time of flight 64 of an acoustic waves traveling against a flow direction of the MFF 68. The second acoustic flow sensor 62 senses a downstream time of flight 66 of acoustic waves traveling with the flow direction of the MFF 68. It is to be understood that that the first acoustic flow sensor 60 and the second acoustic flow sensor 62 may be configured as one unit which senses both the upstream time of flight 64 and the downstream time of flight 66 of acoustic waves traveling through the flow direction of the MFF 68 by having acoustic emitters and detectors at both end of the unit.

The first acoustic flow sensor 60 and the second acoustic flow sensor 62 are located across from each other in staggered position. This configuration of flow sensors is also depicted in FIG. 5. The staggered configuration allows for sensing of acoustic signals that flow both upstream and downstream when emitters and sensors are placed on both ends. A comparison of the upstream and downstream acoustic signals is used to determine the velocity of the MFF flowing through the sensors. The time of flights of the acoustic signals may be compared by one or more processors 17 to determine the velocity of flow or the rate of flow for the MFF.

Figure 7:
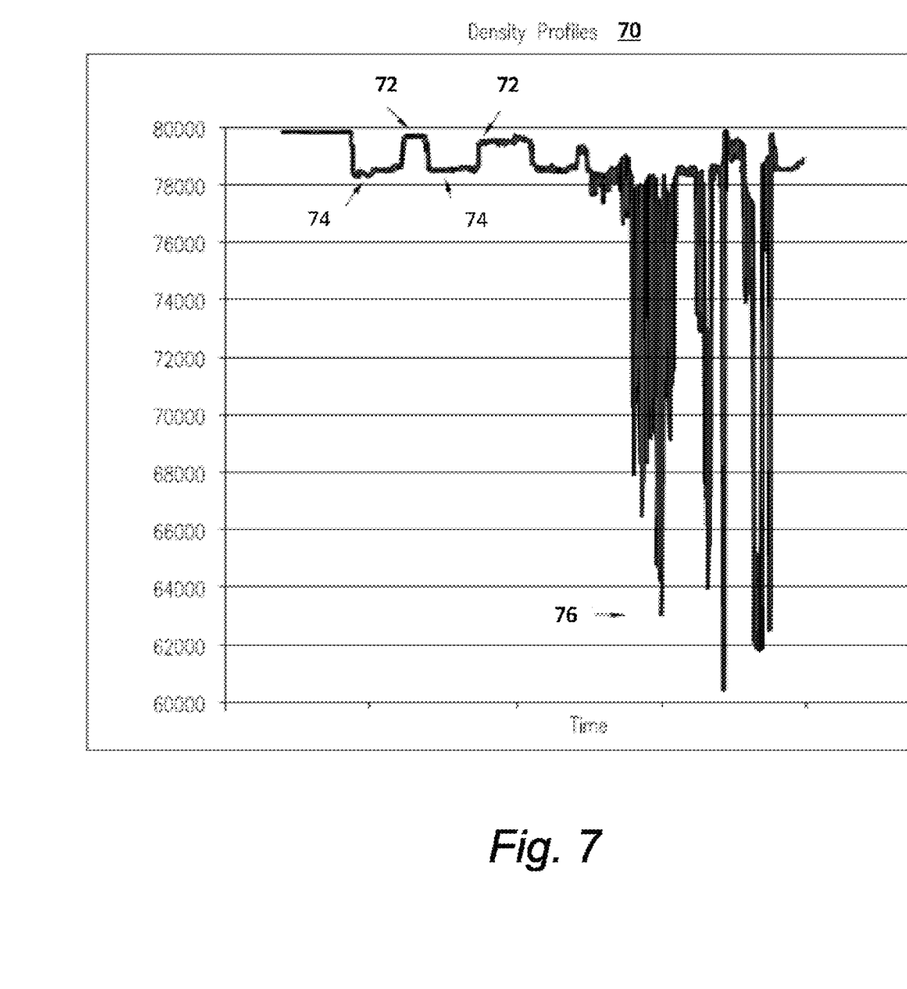
FIG. 7 is an example graph of the first density profiles of a separated MFF taken by the first density sensor of FIG. 1 and/or FIG. 5.

Turning to FIG. 7, density profiles 70 of a separated MFF are shown. The graph of the density profiles 70 is associated with the density profiles taken in real time by the first density sensor 12 of the separated MFF, which is also referred to as a slug flow or a stratified flow. A water density profile 72 is shown as the heaviest of the density profiles followed by the oil density profile 74 which under most conditions is lighter than water. One will understand that under certain temperature and pressure conditions, oil can be heavier than water. The gas density profile 76 is also shown as being lighter than both the water density profile 72 and the oil density profile 74. The graph of density profiles 70 depicts a separated flow of the MFF that alternates between a water phase and an oil phase during the first half of the time interval and transitions to a mostly gas phase during the second half of the time interval. This is typical of a separated flow or a slug flow coming from a well 10 at the position of the first density sensor 12.

Transient analysis is performed on the density profiles 70 by the one or more processors 17 of FIG. 1 and FIG. 5 to determine the water density profile 72, the oil density profile 74, and the gas density profile 76 as shown in FIG. 7. These determinations are then used to determine the density of the oil phase, the density of the water phase, and the density of the gas phase. This density profiles are then used to determine the density of gas, water, and oil by the one or more processors 17.

The third density profile of the third density sensor 16 measures a density profile of a mixed liquid portion of the water and oil mixture that does not contain gas. This density profile would be located between the water density profile 72 and the oil density profile 74 of FIG. 7. Transient analysis is performed on the third density profile to determine the density of the mixed liquid portion of a mixture of water and oil, where the gas phase has separated from the mixed liquid portion. The density of the water and oil mixture is used, along with the density of oil and the density of water, to determine the water cut. The water cut is the ratio of water to oil in the MFF. The one or more processors 17 can be used to determine the densities of the different phases and mixtures of the phases to determine proportions of phases (e.g. water cut and gas volume fraction).

In another example embodiment, the systems 6 and 8 of FIG. 1 and FIG. 5 include a second density sensor 14 that senses in real time. The real time density sensor senses a plurality of second density profiles. The second density sensor 14 may also include at the acoustic waveguide assembly 30 of FIG. 2. The one or more processors may perform transient analysis on the second density profiles to determine an average density of the MFF. The average density may be obtained by placing the second density sensor 14 at the output of the phase mixer-homogenizer 18 of FIG. 1.

Figure 8:
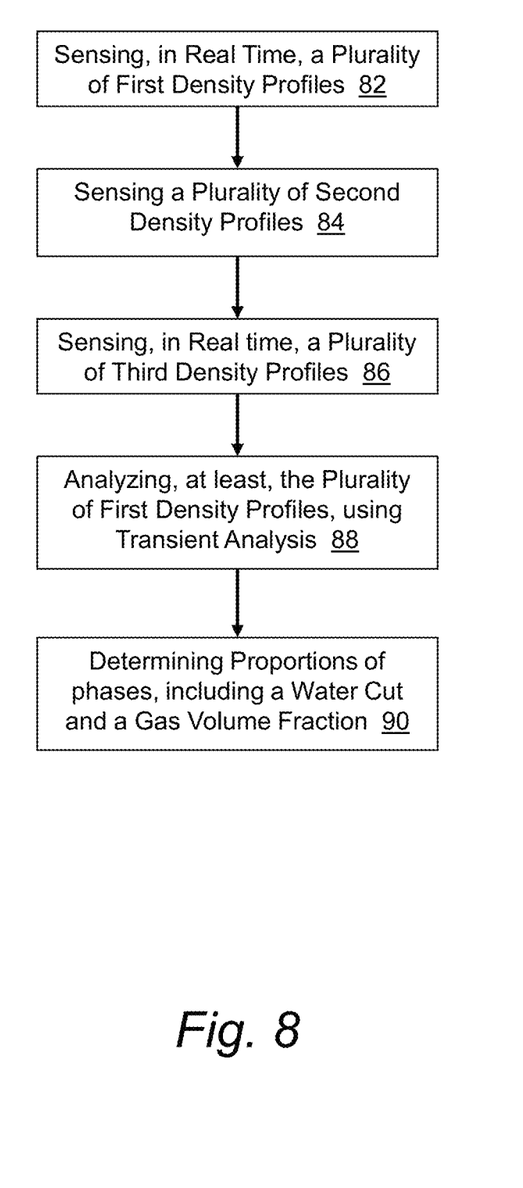
FIG. 8 is an example method for determining densities and proportions of phases in a MFF that can include an oil phase, a water phase, and a gas phase from a well.

Turning to FIG. 8, an example method is shown for determining densities and proportions of phases in a multi-phase fluid flow (MFF) that can include an oil phase, a water phase, and a gas phase from a well. The method includes sensing, in real time, a plurality of first density profiles 82 of the MFF using a first density sensor in a first location where phases of the MFF are, for at least short intervals of time, separated. The method also includes sensing a plurality of second density profiles 84 of the MFF using a second density sensor at a second location where the MFF is a blended mixture of, at least, the oil phase, the water phase, and the gas phase. The method further includes sensing, in real time, a plurality of third density profiles 86 of the MFF using a third density sensor at a third location. The third location is where a gas phase of the MFF is separate from a mixed liquid portion of the MFF that includes at least the water phase and the oil phase. The method also includes analyzing, at least, the plurality of first density profiles, using transient analysis 88, and determining a density of the oil phase, a density of the water phase, and a density of the gas phase. The method also includes determining proportions of phases 90 including a water cut and a gas volume fraction based on the plurality of first, second, and third density profiles.

In another example embodiment, the method of FIG. 8 for determining the proportion of phases includes determining a proportion of the oil phase, a proportion of the water phase, and a proportion of the gas phase based on the water cut and the gas volume fraction. Additionally, the method of determining the proportions of the phases includes determining the water cut and the gas volume fraction.

In yet another example embodiment, the method of FIG. 8 for determining proportions of phases further includes determining an average density of the MFF based on at least a one of the plurality of second density profiles. The method of determining proportions of phases also include determining a density of the mixed liquid portion of the MFF, based on a transient analysis the plurality of third density profiles. The method of determining proportions of phases further includes determining a water cut of the mixed liquid portion of the MFF based on the density of the mixed liquid portion, the density of the water phase of the MFF, and the density of the oil phase. The method for determining proportions of phases also includes determining a gas volume fraction based on, at least, the average density and the density of the gas phase.

In still another example embodiment, the method of FIG. 8 for determining densities and proportions of phases in a multi-phase fluid flow is used with additional steps and/or sequences of an algorithm and data gathering to determine the total output of the individual phases. The additional steps include sensing a velocity or flow rate, with at least a first flow sensor, of the blended mixture. The first flow sensor is located at an output of the phase mixer-homogenizer. The individual phase output quantities are calculated. The individual phase output quantities include one or more of: an output quantity of the oil phase, an output quantity of the water phase, and an output quantity of the gas phase. The output quantities are based, at least in part, on one or more of: phase proportions (e.g. the water cut and the gas volume fraction), an average density of the MFF, the density of the oil phase, the density of the water phase, the density of the gas phase, and the sensed velocity or flow rate of the blended MFF. The density of the oil phase, the density of the water phase, and the density of the gas phase are based on the transient analysis of the plurality of first density profiles.

The invention has been described above with regards to one or more processors that are used to calculate and determine densities, proportions, and quantity outputs of the different phases. The one or more processors include the one or more processors 17 of FIG. 1 and FIG. 5. The one or more processors can include one or more programs that include multiple programs, subroutines, or program sections, hereinafter described as programs. The programs are executed on the one or more processors.

In one example embodiment, the one or more programs include a first program to analyze the plurality of first density profiles, using transient analysis, to determine the density of the oil phase, the density of the water phase, and the density of the gas phase. The plurality of first density profiles are profiles of a separated MFF. The one or more programs also include a second program to determine an average density of the MFF based on at least a one of the plurality of second density profiles. The second program analyzes the plurality of second density signals, using transient analysis, to determine the average density. The one or more programs also include a third program to analyze the plurality of third density profiles, using transient analysis, to determine a density of the mixed liquid portion which includes the water phase and the oil phase as a mixed liquid without the gas phase. The one or more programs further include a fourth program to determine a water cut based on the density of the mixed liquid portion, the density of the oil phase, and the density of the water phase. The one or more programs also include a fifth program to determine a gas volume fraction based on the density of the gas phase and the average density. It is understood that the fourth and fifth program may optionally be used to determine a proportion of the gas phase, a proportion of the water phase, and a proportion of the oil phase in addition to or in place of the water cut and the gas volume fraction.

It is realized that the one or more programs executed on the one or more processors are not limited to a single processor executing a single program. For example, the first program, the second program, and the third program could each be individual programs or may together be parts of a single program with three separate sub-routines. The programs may all be executed on a single processor or multiple processors of the one or more processors. For example, the first program, the second program, and the third program may be executed on a single processor and/or be executed on multiple processors. Additionally, the different programs may be executed on a single processor during a first time period and may be executed on multiple processors during another time period. For example, the one or more processors 17 of FIG. 1 and FIG. 5 can be connected to the first density sensor 12, the second density sensor 14, and the third density sensor 16 either directly or through other devices to receive the first, second, and third density profiles. The density profiles are then provided to the one or more programs which perform transient analysis on the density profiles to determine the different densities and the proportions of the different phases in the MFF.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A system for determining densities and proportions of phases in a multi-phase fluid flow (MFF) that can include an oil phase, a water phase, and a gas phase from a well, the system including:
   a first density sensor that senses, in real time, a plurality of first density profiles of the MFF at a first location where phases of the MFF are separated for, at least, short intervals of time;
   a second density sensor that senses a plurality of second density profiles of the MFF at a second location where the MFF is a blended mixture of, at least, the oil phase, the water phase, and the gas phase;
   a third density sensor that senses, in real time, a plurality of third density profiles of the MFF at a third location where the gas phase is separate from a mixed liquid portion of the MFF that includes, at least, the water phase and the oil phase; and one or more processors for executing one or more programs to determine a density of the oil phase, a density of the water phase, a density of the gas phase, and proportions of phases including a water cut and a gas volume fraction based on at least the plurality of first, second, and third density profiles.

2. The system according to claim 1, wherein the MFF comes from a high pressure well that includes one or more of: a gas well, an oil well, and a petroleum well.

3. The system according to claim 1,
wherein the first location of the first density sensor is upstream of a phase mixer-homogenizer,
wherein the second location of the second density sensor is at an output of the phase mixer-homogenizer that homogenizes the MFF into the blended mixture, and
wherein the third location of the third density sensor is downstream of the phase mixer-homogenizer and where mixing is maintained between at least the water phase and the oil phase of the mixed liquid portion.

4. The system according to claim 1, wherein the one or more programs executed on the one or more processors include:
a first program to analyze the plurality of first density profiles, using transient analysis, to determine the density of the oil phase, the density of the water phase, and the density of the gas phase,
a second program to determine an average density of the MFF based on at least a one of the plurality of second density profiles,
a third program to analyze the plurality of third density profiles, using transient analysis, to determine a density of the mixed liquid portion,
a fourth program to determine a water cut based on the density of the mixed liquid portion, the density of the oil phase, and the density of the water phase, and
a fifth program to determine a gas volume fraction based on the density of the gas phase and the average density.

5. The system according to claim 1, further including:
at least one flow sensor that senses a velocity of the blended mixture,
wherein the one or more processors for executing one or more programs is also to determine an output quantity of the oil phase, an output quantity of the water phase, and an output quantity of the gas phase based, at least, on the density of the oil phase, the density of the water phase, the density of the gas phase, the proportions of phases, and the velocity of the blended mixture; and
an interface to output to a user, at least, one of: the output quantity of the oil phase, the output quantity of the water phase, and the output quantity of the gas phase.

6. The system according to claim 5, wherein the at least one flow sensor further includes:
an acoustic flow sensor that senses, at least, an upstream time of flight of acoustic waves traveling against a flow direction of the MFF and a downstream time of flight of acoustic waves traveling with the flow direction of the MFF.

7. The system according to claim 1,
wherein at least the first and third density sensors that sense, in real time, each include at least one acoustic waveguide assembly,
an acoustic waveguide assembly, further including:
a waveguide rod having a proximal end and a distal end, wherein at least a portion of the waveguide rod is to be immersed in the MFF; and
a waveguide sensor connected to the distal end of the waveguide rod for sensing a plurality of time of flights of acoustic signals reflected off, at least, the proximal end of the waveguide rod,
wherein a one of the plurality of time of flights of acoustic signals is used to determine a density profile of a first fluid section of the MFF, and
wherein the waveguide rod is immersed in the first fluid section when the one of the plurality of time of flights of acoustic signals is sensed by the waveguide sensor.

8. The system according to claim 7,
wherein the waveguide rod has a first cross section at the distal end and a second cross section at the proximal end,
wherein a portion of the waveguide rod is immersed in the MFF,
wherein the waveguide sensor senses a first time of flight of a first portion of an acoustic signal that hits an end of the waveguide rod with the first cross section and reflects back to the waveguide sensor and senses a second time of flight of a second portion of the acoustic signal that hits an end of the waveguide rod with the second cross section and reflects back to the waveguide sensor, and
wherein the one or more processors is to also compare the first time of flight and the second time of flight to determine a density profile.

9. The system according to claim 8, wherein the acoustic waveguide assembly is configured to be mounted on a conduit that conducts a high pressure MFF.

10. The system according to claim 8,
wherein the second density sensor senses, in real time, the plurality of second density profiles,
wherein the second density sensor includes at least one acoustic wave guide assembly, and
wherein an another program, performed on the one or more processors, is to analyze the plurality of second density profiles, using transient analysis, to determine an average density of the MFF.

11. A method for determining densities and proportions of phases in a multi-phase fluid flow (MFF) that can include an oil phase, a water phase, and a gas phase from a well, the method including:
sensing, in real time, a plurality of first density profiles of the MFF using a first density sensor at a first location where phases of the MFF are, for at least short intervals of time, separated;
sensing a plurality of second density profiles of the MFF using a second density sensor at a second location where the MFF is a blended mixture of, at least, the oil phase, the water phase, and the gas phase;
sensing, in real time, a plurality of third density profiles of the MFF using a third density sensor at a third location, wherein the third location is where a gas phase of the MFF is separate from a mixed liquid portion of the MFF that includes at least the water phase and the oil phase;
analyzing, at least, the plurality of first density profiles, using transient analysis, and determining a density of the oil phase, a density of the water phase, and a density of the gas phase; and
determining proportions of phases including a water cut and a gas volume fraction based on the plurality of first, second, and third density profiles.

12. The method according to claim 11, wherein said determining the proportions of phases including the water cut and the gas volume fraction further includes:
determining an average density of the MFF based on at least a one of the plurality of second density profiles, determining a density of the mixed liquid portion of the MFF, based on a transient analysis of the plurality of third density profiles, determining a water cut of the mixed liquid portion of the MFF based on the density of the mixed liquid portion, the density of the water phase of the MFF, and the density of the oil phase, determining a gas volume fraction based on, at least, the average density and the density of the gas phase.

13. The method according to claim 11, further including:
locating the first density sensor at the first location that is upstream of a phase mixer-homogenizer where phases are separated;
locating the second density sensor at a second location that is at an output of the phase mixer-homogenizer that homogenizes the MFF into the blended mixture; and
locating the third density sensor at a third location that is downstream of the phase mixer-homogenizer, wherein the third location is where mixing is maintained between at least the water phase and the oil phase of the mixed liquid portion.

14. The method according to claim 13, wherein said sensing the plurality of first and third density profiles, in real time, further includes:
sending an acoustic signal down a waveguide rod with a first cross section at a distal end and a second cross section at a proximal end;
sensing a first time of flight of a first portion of the acoustic signal that hits an end of the first cross section and reflects back to a waveguide sensor;
sensing a second time of flight of a second portion of the acoustic signal that hits an end of the second cross section and reflects back to the waveguide sensor;
comparing the first time of flight and the second time of flight to determine one or more of the plurality of first density profiles and the plurality of third density profiles; and
iteratively repeating said sending the acoustic signal and said sensing of the first and second time of flights to obtain one or more of the plurality of first density profiles and the plurality of third density profiles,
wherein a portion of the waveguide rod is immersed in the MFF.

15. The method according to claim 14, further including:
sending the acoustic signal down the waveguide rod with a transducer,
wherein an interior portion of the waveguide rod is configured to withstand a high pressure environment within a conduit that contains the MFF, and
wherein a high pressure coupler connects the conduit and the waveguide rod and forms a high pressure seal between the interior portion of the waveguide rod that is located within the conduit and an exterior portion of the waveguide rod that is located outside of the conduit where the transducer is attached to the waveguide rod.

16. The method according to claim 13, further including:
sensing a velocity, with at least a first flow sensor, of the blended mixture, wherein the first flow sensor is located at an output of the phase mixer-homogenizer.

17. The method according to claim 16, wherein the phase mixer-homogenizer that mixes the phases of the MFF to cause flow rates of the oil phase, the water phase, and the gas phase to have uniform rates of flow.

18. The method according to claim 16, wherein said sensing the velocity further includes:
sensing an upstream time of flight of acoustic waves traveling against a flow direction of the MFF,
sensing a downstream time of flight of acoustic waves traveling with the flow direction of the MFF, and
calculating the velocity of the MFF based, at least in part, on the upstream time of flight and the downstream time of flight,
wherein the first flow sensor is an acoustic flow sensor.

19. The method according to claim 16, further including:
calculating individual phase output quantities including: an output quantity of the oil phase, an output quantity of the water phase, and an output quantity of the gas phase based, at least in part, on the water cut, the gas volume fraction, an average density of the MFF, the density of the oil phase, the density of the water phase, and the density of the gas phase, and
wherein the density of the oil phase, the density of the water phase, and the density of the gas phase are based on the transient analysis of the plurality of first density profiles.

20. A system for determining output quantities of phases in a multi-phase fluid flow (MFF) that can include an oil phase, a water phase, and a gas phase from a well, by determining densities and proportions of phases in the MFF, the system including:
a first density sensor that senses, in real time, a plurality of first density profiles of the MFF at a first location where phases of the MFF are separated for, at least, short intervals of time;
a second density sensor that senses a plurality of second density profiles of the MFF at a second location where the MFF is a blended mixture of, at least, the oil phase, the water phase, and the gas phase, wherein the second location of the second density sensor is at an output of a phase mixer-homogenizer that homogenizes the MFF into the blended mixture;
a third density sensor that senses, in real time, a plurality of third density profiles of the MFF at a third location where the gas phase is separate from a mixed liquid portion of the MFF that includes, at least, the water phase and the oil phase;
at least one flow sensor that senses a velocity of the blended mixture; and
one or more processors for executing one or more programs to determine a density of the oil phase, a density of the water phase, a density of the gas phase, and proportions of phases based on at least the plurality of first, second, and third density profiles,
the one or more processors for executing one or more programs is also to determine and output to a user one or more of: an output quantity of the oil phase, an output quantity of the water phase, and an output quantity of the gas phase based, at least, on the velocity of the blended mixture, the density of the oil phase, the density of the water phase, the density of the gas phase, and the proportions of phases.

* * * * *